(12) United States Patent
Wilkinson et al.

(10) Patent No.: US 7,159,714 B2
(45) Date of Patent: Jan. 9, 2007

(54) SHARPS TRANSPORT AND DISPOSAL SYSTEM

(75) Inventors: Bradley M. Wilkinson, North Haledon, NJ (US); Hugh T. Conway, Verona, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 10/372,560

(22) Filed: Feb. 21, 2003

(65) Prior Publication Data
US 2004/0163982 A1 Aug. 26, 2004

(51) Int. Cl.
*B65D 83/10* (2006.01)

(52) U.S. Cl. .................. 206/366; 206/567; 206/571

(58) Field of Classification Search ............ 206/364, 206/366, 370, 359, 372–375, 368, 570, 571, 206/438, 501, 557, 567, 167, 169; D24/131; 220/23.83, 23.86
See application file for complete search history.

(56) References Cited

U.S. PATENT DOCUMENTS

| | | | | |
|---|---|---|---|---|
| 75,689 | A * | 3/1868 | Mattson | 206/364 |
| 4,195,734 | A * | 4/1980 | Boner et al. | 206/560 |
| D265,125 | S * | 6/1982 | Jordan | D24/131 |
| 4,658,957 | A * | 4/1987 | Guth et al. | 206/366 |
| 4,863,451 | A * | 9/1989 | Marder | 206/366 |
| 4,895,256 | A * | 1/1990 | Johnston | 206/349 |
| 4,984,686 | A | 1/1991 | Shillington | |
| 5,011,013 | A * | 4/1991 | Meisner et al. | 206/373 |
| 5,024,326 | A | 6/1991 | Sandel et al. | |
| 5,184,720 | A | 2/1993 | Packer et al. | |
| 5,441,163 | A * | 8/1995 | Carrasco | 206/506 |
| 5,447,237 | A * | 9/1995 | Carter et al. | 206/570 |
| 5,575,401 | A * | 11/1996 | Trower et al. | 206/379 |
| 5,630,506 | A | 5/1997 | Thorne et al. | |
| 5,706,942 | A | 1/1998 | Vila et al. | |
| 5,938,063 | A | 8/1999 | Hoftman | |
| 6,024,216 | A | 2/2000 | Shillington et al. | |
| 6,283,909 | B1 | 9/2001 | Sharp | |
| 2001/0019023 | A1 | 9/2001 | Britton et al. | |
| 2002/0014560 | A1 | 2/2002 | Diamond | |
| 2004/0040874 | A1 * | 3/2004 | Chen Chen | 206/373 |

FOREIGN PATENT DOCUMENTS

| | | |
|---|---|---|
| DE | 35 06 218 A1 | 8/1986 |
| DE | 41 36 171 A1 | 6/1993 |
| EP | 0 242 035 A1 | 10/1987 |
| GB | 2 338 230 A | 12/1999 |
| WO | WO 00/32114 | 6/2000 |

* cited by examiner

*Primary Examiner*—Mickey Yu
*Assistant Examiner*—J. Gregory Pickett
(74) *Attorney, Agent, or Firm*—Jeanne P. Lukasavage

(57) ABSTRACT

The present invention is directed to a medical transport carrier, as well as a medical waste disposal container. The medical transport carrier includes a carrier tray and a medical waste disposal container. The carrier tray includes a supply area adapted for containing medical supplies. The medical waste disposal container is interengagably and removably mated with the carrier tray and is located at a location remote from the supply area. The present invention is also directed to a medical waste disposal container adapted for engaging with a carrier tray having a supply area for containing medical supplies. The medical waste disposal container is interengagably and removably matable with the carrier tray and is adapted for containing medical waste at a location remote from the supply area of the carrier tray.

13 Claims, 7 Drawing Sheets

SHARPS TRANSPORT AND DISPOSAL SYSTEM

BACKGROUND OF THE INVENTION

1. Field of the Invention

The present invention relates to a container assembly. More particularly, the present invention relates to a container assembly including a medical waste disposal container for use with a portable carrier tray for medical instruments.

2. Description of Related Art

Typical blood collection procedures require phlebotomists to organize medical supplies, such as needles, holders, tubes, and bandages, in a transportable utility carrier. The utility carrier typically has a handle, includes an opening at the top, and may have multiple sections or compartments to aid in the organization of medical supplies. The utility carrier allows for convenient transportation of medical supplies.

Typically, a phlebotomist carries a portable tray, such as a utility carrier, to a patient's bedside where the phlebotomist performs the necessary procedure, such as a blood collection procedure. When the required necessary tubes are collected and the needle is withdrawn from the patient's arm, the phlebotomist immediately discards the used blood collection device into a container at the immediate site in order to prevent re-use of the device and to protect from potentional biohazards.

Such used devices, commonly referred to as sharps, are often discarded in a small medical waste container that fits onto the utility tray. Recently, however, there is a trend in the industry to use blood collection assemblies that incorporate disposable needle holders used in combination with disposable needles, and recent changes in regulations and safety procedures are calling for the needle holder to be discarded as well. The use of such assemblies involves significantly more medical waste being discarded into medical waste containers. As such, portable waste containers carried with utility trays are oftentimes too small to contain the disposable assemblies, or cannot contain a significant amount of disposable waste, therefore resulting in frequent changing of the disposable waste container.

An alternate medical waste container commonly used is the type mounted on the wall, such as in the patient's room. However, the use of such wall mounted containers to discard used blood collection devices in such procedures increases the risk of exposure to biohazards, since the waste container is remotely located from the site of use of the medical device, requiring transport of the used device to the remotely located waste container. Another commonly used medical waste container is relatively large and is primarily intended for lab use where it is placed on the floor or table. Such large lab waste containers involve similar exposure risks, due to the remote location of the waste container from the site of use.

Therefore, a need exists for a device in which to transport medical supplies to the patient for use in medical procedures while allowing for the convenient use, safe transportation, and disposing of volumes of hazardous waste, such as used sharps, at the primary point of care.

SUMMARY OF THE INVENTION

The present invention is directed to a medical transport carrier, as well as a medical waste disposal container. The medical transport carrier includes a carrier tray and a medical waste disposal container. The carrier tray includes a supply area adapted for containing medical supplies. The medical waste disposal container is interengagably and removably mated with the carrier tray and is located at a location remote from the supply area. As such, the medical waste disposal container is available at the point of use or point of care, and is capable of containing medical waste at a location which is associated with the point of use of the device but remote from the supply area of the device, thereby avoiding exposure to unused supplies.

Desirably, the carrier tray is in engagement with the medical waste disposal container and includes an opening for disposing of medical waste through the carrier tray and into an opening in the medical waste disposal container via a connecting passageway. The medical waste disposal container may be detachable from the carrier tray and may be located below the carrier tray. The medical waste disposal container further may include an integrated handle which extends through an opening in the carrier tray. The opening of the medical waste disposal container may be adjacent the opening in the carrier tray which is provided for receiving the carry handle.

In a further embodiment, the present invention is directed to a medical waste disposal container adapted for engaging with a carrier tray having a supply area for containing medical supplies. The medical waste disposal container is interengagably and removably matable with a carrier tray and adaptable for containing medical waste at a location remote from the supply area of the carrier tray. The medical waste disposal container may have an opening for receiving medical waste, with the opening forming a connecting passageway with an opening in the carrier tray. The medical waste disposal container may also include an integrated handle which extends through an opening in the carrier tray, and which may be foldable for storage and disposal.

DETAILED DESCRIPTION

Figure 1:
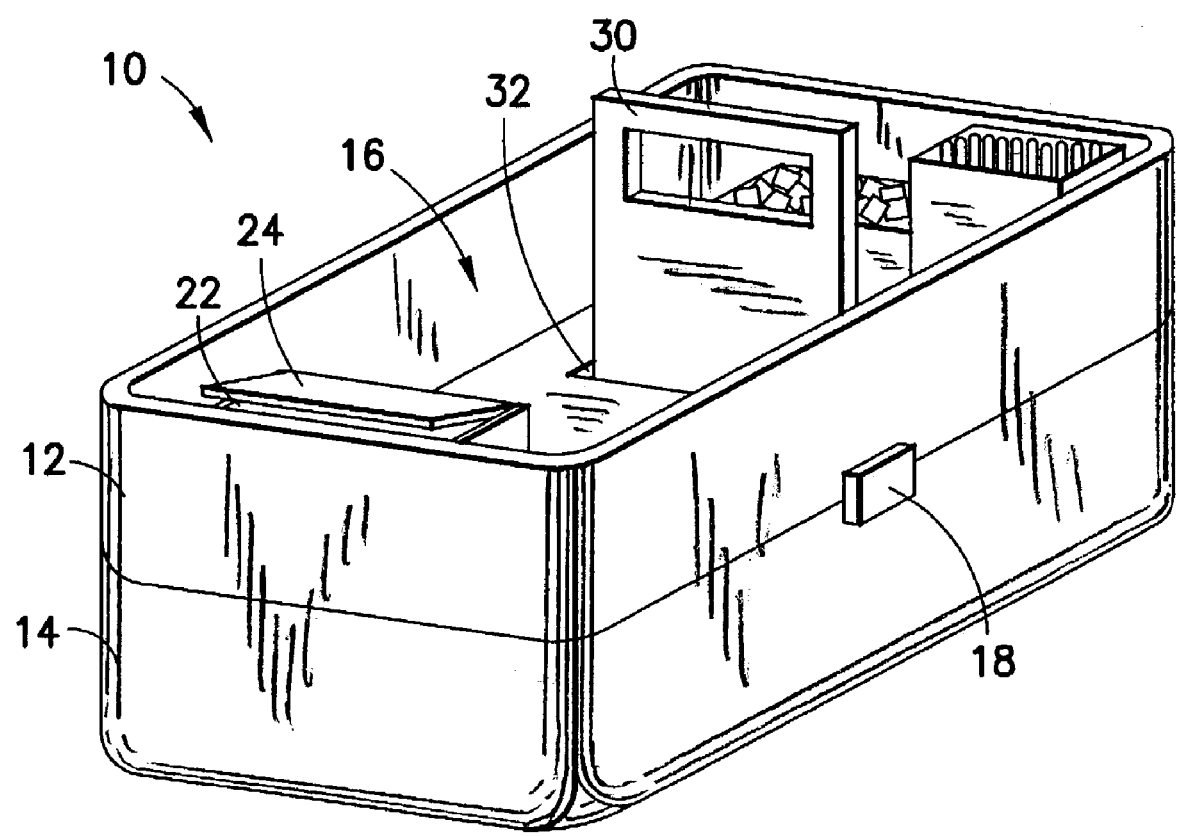
FIG. 1 is a schematic view of a medical transport carrier in accordance with the present invention.

Referring to the drawings in which like reference characters refer to the like parts throughout the several views thereof, FIG. 1 illustrates a medical transport carrier 10 in accordance with the present invention and the related features. The present invention is generally described in terms of a medical transport carrier, and encompasses such a medical transport carrier as well as a medical waste disposal container for use in such a medical transport carrier.

Figure 2:
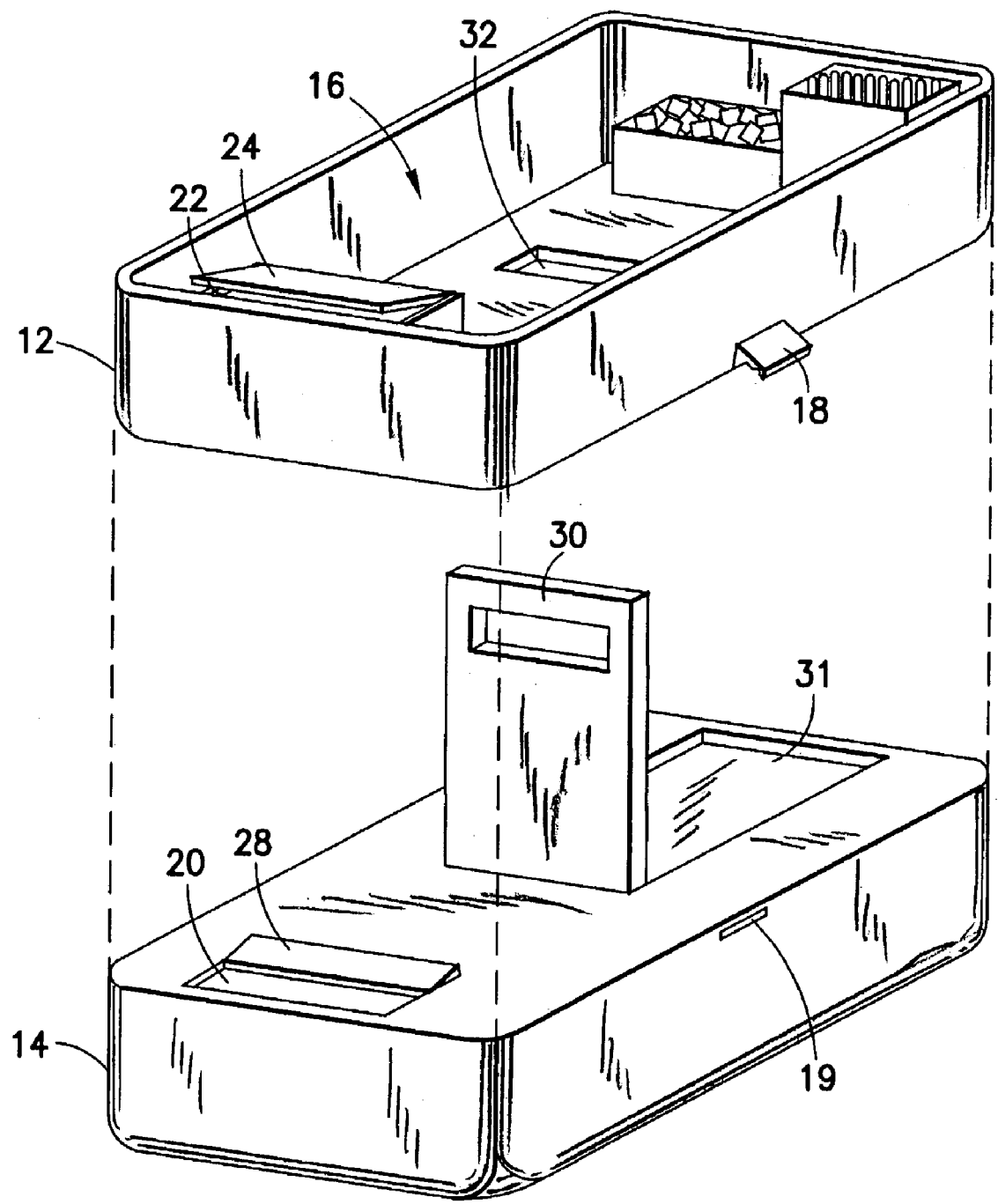
FIG. 2 is a schematic view of the medical transport carrier of the present invention showing a medical waste disposal container separated from a carrier tray.

As shown in FIGS. 1 and 2, a medical transport carrier 10 includes a carrier tray 12 and a medical waste disposal container 14. The carrier tray 12 includes a supply area 16 that is adapted for containing medical supplies. The medical waste disposal container 14 is mated with carrier tray 12, and is desirably a separate member which is removably mated with carrier tray 12. As such, the medical waste disposal container is available for use by the technician at the point of use or point of care, and is capable of containing medical waste at a location which is associated with the point of use of the device but remote from the supply area of the device, thereby avoiding exposure to unused supplies. For purposes of the present invention, the term "remote" means a location which is associated with, nearby or next to an area but which is not directly positioned within that area. For example, the medical waste disposal container is located near the supply area but is not directly in the supply area, and therefore medical supplies within the supply area of the container are not directly exposed to medical waste within the medical waste disposal container.

The carrier tray 12 can be made of any material, but preferably is made of molded plastic. The material is durable in nature, thus allowing for prolonged use. Carrier tray 12 has an open top so as to provide convenient accessibility to the supplies located within carrier tray 12. Additionally, carrier tray 12 can include a plurality of compartments or sections of varying shapes and sizes within supply area 16 to aid in the organization of medical supplies. Such medical supplies include, for example, needles, needle holders, blood collection tubes, swabs, bandages, lancets and the like. Carrier tray 12 can also have various surface textures, such as grips to facilitate convenient separation from medical waste disposal container 14 and lifting of carrier tray 12. Alternate embodiments are also possible with various features to aid in convenient organization and transportation of supplies.

Medical transport carrier 10 further includes medical waste disposal container 14, which is configured and designed for containing and disposing of used medical instruments such as sharps. Medical waste disposal container 14 is constructed of a material capable of safely containing such used sharps, and may be made of molded plastic, such as through blow molding or flow molding for durability. Medical waste disposal container 14 is interengagably mated with carrier tray 12 so that it can be transported as a one-piece unit, and is desirably removably mated with carrier tray 12. For example, medical waste disposal container 14 may mate with the bottom surface of carrier tray 12 to form an integral structure, as shown in FIG. 1.

Medical waste disposal container 14 and carrier tray 12 may include corresponding structure for mating engagement therebetween, and desirably for locking engagement therebetween. Desirably, such locking engagement is temporary in nature so that carrier tray 12 is secured in a removable or releasable fashion and is not damaged, thereby allowing repetitive usage. As shown in FIG. 2, such corresponding structure may include a latch 18 on an outer surface of carrier tray 12, and a corresponding rib 19 on an outer surface of medical waste disposal container 14. It is contemplated that a second latch and rib may be provided on the opposing side of carrier tray 12 and medical waste disposal container 14. Latch 18 engages with rib 19 to integrally lock carrier tray 12 and medical waste disposal container 14 together, and latch 18 can be released from rib 19 to detachably release tray 12 from locking engagement with medical waste disposal container 14. It is noted that the rib and latch are discussed merely as an exemplary method of removably mating the carrier tray 12 and the medical waste disposal container 14, and other means for releasable mating engagement therebetween are contemplated by the present invention.

As noted, medical waste disposal container 14 may mate with the bottom surface of carrier tray 12. As such, medical waste disposal container 14 should have sufficient structural integrity to be able to support the weight of carrier tray 12 when filled with appropriate medical supplies for use. Such structural integrity may be provided through a specific shape, design, material of construction, or supporting features provide with medical waste disposal container 14. It is further noted that medical waste disposal container 14 and carrier tray 12 may include different "footprints", i.e., may be of different shapes or sizes. For instance, medical waste disposal container 14 may be slightly smaller than the overall size of carrier tray 12 and may fit within a bottom area of carrier tray 12 to conceal it from view. In such an embodiment, carrier tray 12 may include an area for accommodating medical waste disposal container 14, such as a perimetrical skirt extending from the bottom perimeter of carrier tray 12.

Figure 3:
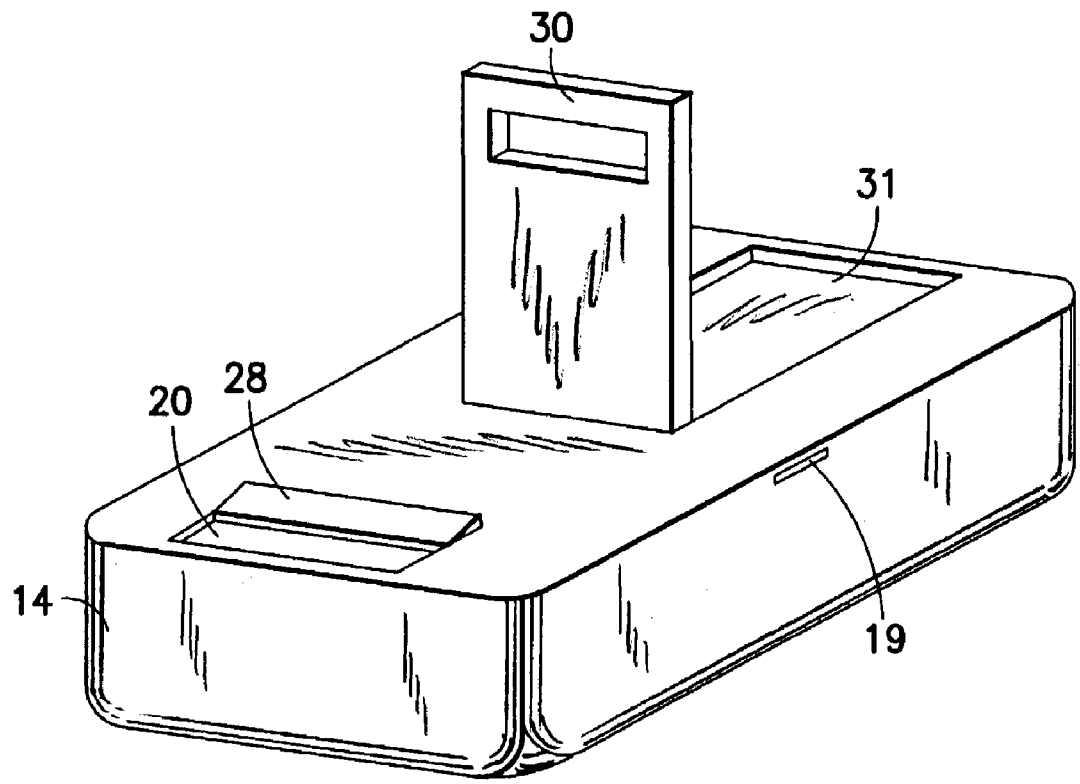
FIG. 3 is a schematic top view of a medical waste disposal container in accordance with the present invention.
Figure 4:
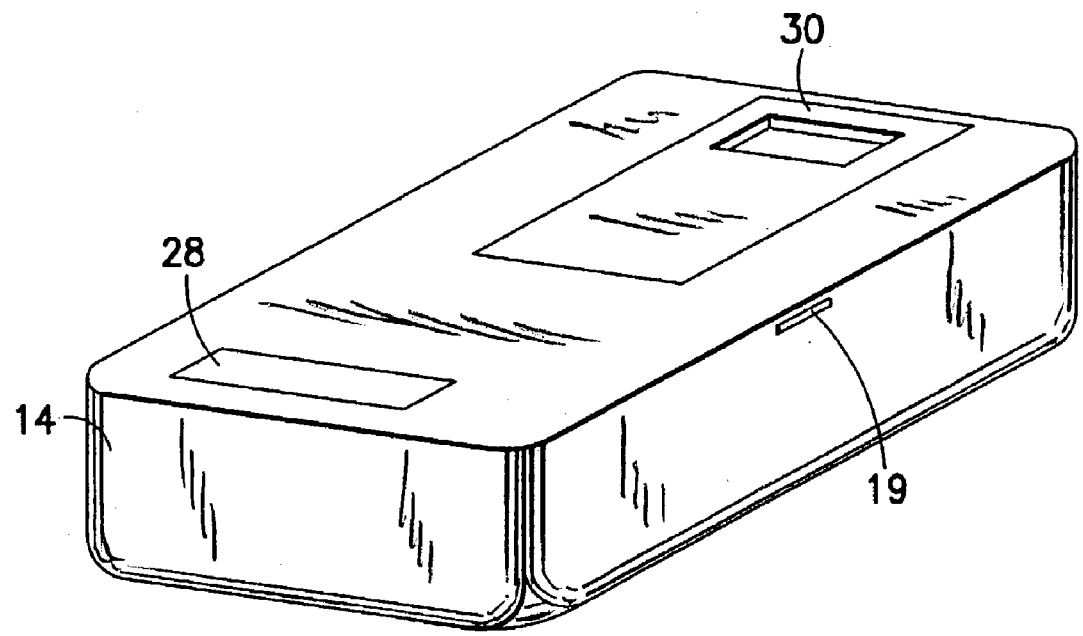
FIG. 4 is a schematic top view of a medical waste disposal container with the integrated handle in a folded position.

A handle is further provided for carrying medical transport carrier 10. The handle may be associated with either carrier tray 12 or with medical waste disposal container 14. Desirably, medical waste disposal container 14 has an integrated handle 30 or carry handle in a center area of the medical waste disposal container 14, as shown in FIGS. 3–4. Carrier tray 12 has an open slot area 32 for receiving handle 30 of medical waste disposal container 14 therethrough. As such, carrier tray 12 may be placed directly atop medical waste disposal container 14 so that open slot area 32 in carrier tray 12 corresponds and aligns with handle 30 of medical waste disposal container 14. Handle 30 then passes and extends through and above open slot area 32 of carrier tray 12. Once carrier tray 12 is firmly in place atop medical waste disposal container 14, carrier tray 12, and medical waste disposal container 14 can be secured together to form medical transport carrier 10. Handle 30 of medical waste disposal container 14 allows for medical transport carrier 10 to be conveniently and safely handled and transported, as well as assures secure attachment of carrier tray 12 to medical waste disposal container 14. As shown in FIG. 4, handle 30 of medical waste disposal container 14 may be collapsible or foldable, thus allowing for numerous medical waste disposal containers to be stacked upon each other to allow for convenient and efficient storage and transport. The top surface of medical waste disposal container 14 may include a recess 31 for accommodating handle 30 when in a folded position.

As indicated, medical waste disposal container 14 is designed to contain medical waste, such as sharps, for disposal thereof. Medical waste disposal container 14 may have an open top configuration for mating with the bottom surface of carrier tray 12, so long as a closed waste disposal unit is provided when carrier tray 12 and medical waste disposal container 14 are mated. In such an embodiment, a separate lid may be provided for closing medical waste disposal container 14 after separation from carrier tray 12 for proper disposal thereof.

More desirably, medical waste disposal container 14 is a closed unit for containing medical waste, and includes an opening for receiving the medical waste, such as opening 20. Desirably, opening 20 provides a one-way opening through which medical waste can be deposited within medical waste disposal container 14, which may be achieved through a tortuous path into the interior portion thereof, or through a one-way door extending over opening 20.

Opening 20 can be located anywhere on medical waste disposal container 14, so long as medical waste can be deposited through opening 20 while carrier tray 12 is attached to medical waste disposal container 14. Desirably, opening 20 is located on a top surface of medical waste disposal container 14. As such, it is necessary to provide access to opening 20 through carrier tray 12. This is desirably achieved by also providing an opening 22 through carrier tray 12. As such, carrier tray 12 and medical waste disposal container 14 are interengagably mated such that a connecting passageway is established between opening 22 of carrier tray 12 and opening 20 of medical waste disposal container 14, thus providing an area through which medical waste can be disposed and received in medical waste disposal container 14. Desirably, opening 22 of carrier tray 12 is directly aligned with opening 20 of medical waste disposal container 14.

As shown in FIG. 1, opening 22 desirably extends through a top portion of carrier tray 12 and through a bottom portion of carrier tray 12. Desirably, opening 22 is a controlled opening which includes one-way features to prevent sharps from spilling out of medical waste disposal container 14. For example, a lid or protective covering 24 may be provided to close the opening 22. Protective covering 24 provides additional protection to the phlebotomist from being exposed or injured by any medical waste which may extend or protrude from opening 22 of carrier tray 12. The protective covering 24 can be of any type, such as a swinging flap on hinges or the like. Desirably, opening 22 is located along the length of one side of carrier tray 12 as shown in FIG. 1. Alternatively, opening 22 of carrier tray 12 can be an open slot which directly connects with opening 20 of medical waste disposal container 14.

Opening 20 of medical waste disposal container 14 may also have a lid or protective covering 28 to seal the contents within medical waste disposal container 14, particularly after medical waste disposal container 14 is separated from carrier tray 12. Covering 28 of opening 20 of medical waste disposal container 14 can utilize any securing mechanisms such as hinges, tabs, and the like to secure the contents within medical waste disposal container 14. Desirably, opening 20 of medical waste disposal container 14 is capable of automatically opening when carrier tray 12 and medical waste disposal container 14 are mated. For example, covering 28 may open inwardly within opening 20, and carrier tray 12 may include structure on the bottom thereof which engages covering 28 and automatically pushes covering 28 inwardly within opening 20 when carrier tray 12 is mated with medical waste disposal container 14, thereby maintaining covering 28 open. It is noted that carrier tray 12 in such an embodiment should provide effective covering to prevent exposure to the contents of medical waste disposal container 14.

Figure 10:
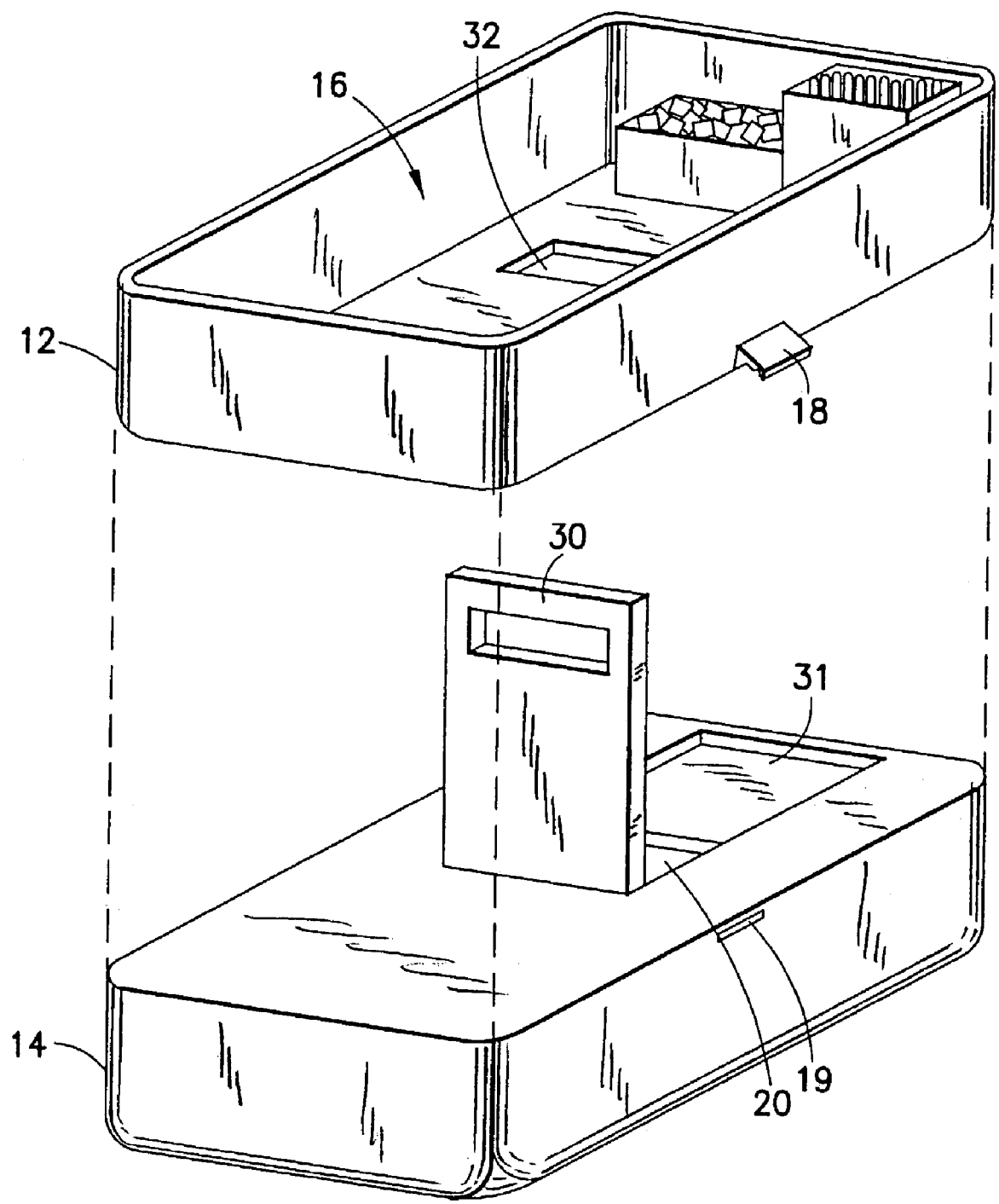
FIG. 10 is a schematic view of a medical transport carrier in a further embodiment of the present invention showing a medical waste disposal container separated from a carrier tray.

As noted above, carrier tray 12 desirably sits on top of medical waste disposal container 14, with handle 30 extending through opening 32 in carrier tray 12. In a particularly desirable embodiment as shown in FIG. 10, opening 20 within medical waste disposal container 14 is adjacent handle 30, and aligns with opening 32 in carrier tray 12 when carrier tray 12 is mated with medical waste disposal container 14 with handle 30 extending through opening 32. In such an embodiment, opening 32 is capable of accommodating handle 30, and further provides a connecting passageway with opening 20 of medical waste disposal container 14, thereby acting as the opening in carrier tray 12 through which medical waste can be disposed, and eliminating the need for a separate opening 22. It is also contemplated that handle 30 may act as a protective covering for sealing opening 20 of medical waste disposal container 14. More particularly, when carrier tray 12 and medical waste disposal container 14 are separated, handle 30 may be folded down and may cover opening 20, thereby acting as a protective cover to seal the contents of medical waste disposal container 14.

Medical waste disposal container 14 may also have foam or other liners at the bottom or on the walls to minimize noise. Alternatively, the medical waste disposal container 14 may have an expandable feature such as a bellows or telescoping portion in which case, the bellows may be blow molded while the components for telescoping may be formed as an assembly of injection molded parts. Medical waste disposal container 14 can also include a translucent wall section or, alternatively, can be constructed entirely of a translucent material, to allow for viewing of the contents of medical waste disposal container 14 and ascertain the need to replace medical waste disposal container 14. Additionally, medical waste disposal container 14 can have fill lines to indicate the maximum capacity of medical waste disposal container 14 and the need to replace the filled medical waste disposal container with an empty medical waste disposal container. Further features of medical waste disposal container 14 may include color coding or special labels or bar codes.

By providing medical waste disposal container 14 integrated with carrier tray 12 and by providing an opening 20 therein for disposing of medical waste, medical transport carrier 10 provides an effective all-in-one unit for performing medical procedures and for disposing of medical waste at a location remote and separate from the sterilized medical supplies. For example, a medical technician such as a phlebotomist can store and use medical supplies such as a blood collection assembly in the supply area 16 of carrier tray 12, and can discard the used supplies through opening 22 and through opening 20 into medical waste disposal container 14, thereby effectively containing the used medical waste at a location remote from the supply area 16 of carrier tray 12, but integral with the carrier tray 12. Moreover, by providing medical waste disposal container 14 as a removable element which is integral with the carrier tray, the medical waste disposal container 14 can be designed so as to contain larger amounts of medical waste, and carrier tray 12 can be re-used.

Figure 5:
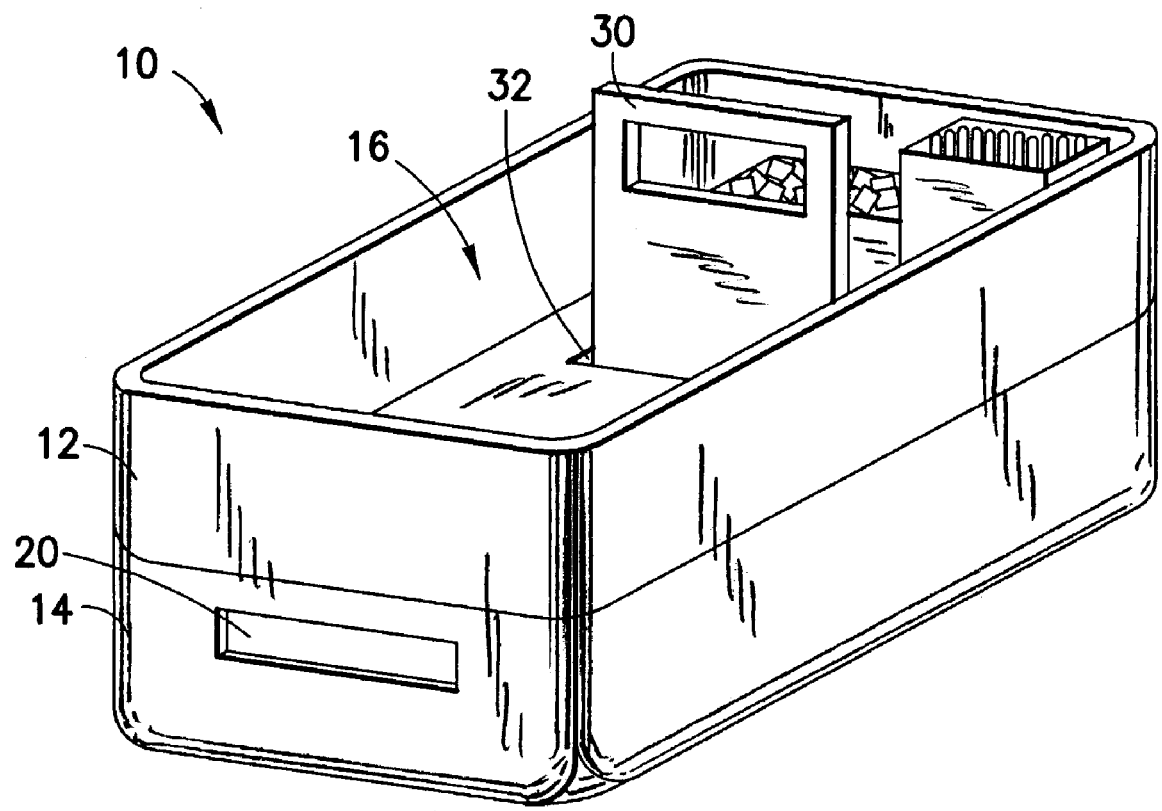
FIG. 5 is a schematic view of a medical transport carrier in accordance with another embodiment of the present invention.

In an alternate embodiment of the present invention depicted in FIG. 5, the medical transport carrier 10 can include a medical waste disposal container 14 with opening 20 on a side of medical waste disposal container 14. Opening 20 in medical waste disposal container 14 can be located on any side of the medical waste disposal container 14 and alleviates the need for medical waste to travel through carrier tray 12 to be collected in medical waste disposal container 14. Instead, the medical waste is deposited directly into medical waste disposal container 14 through opening 20. As such, medical waste is directly deposited in medical waste disposal container 14, and upon filling, medical waste disposal container 14 is detached from carrier tray 12 and is replaced.

FIGS. 6–9 depict further embodiments of the invention that include many components which are substantially identical to the components of FIGS. 1–5. Accordingly, similar components performing similar functions will be numbered identically to those components of FIGS. 1–5, except that a suffix "a" will be used to identify those similar components in FIGS. 6–9.

Figure 6:
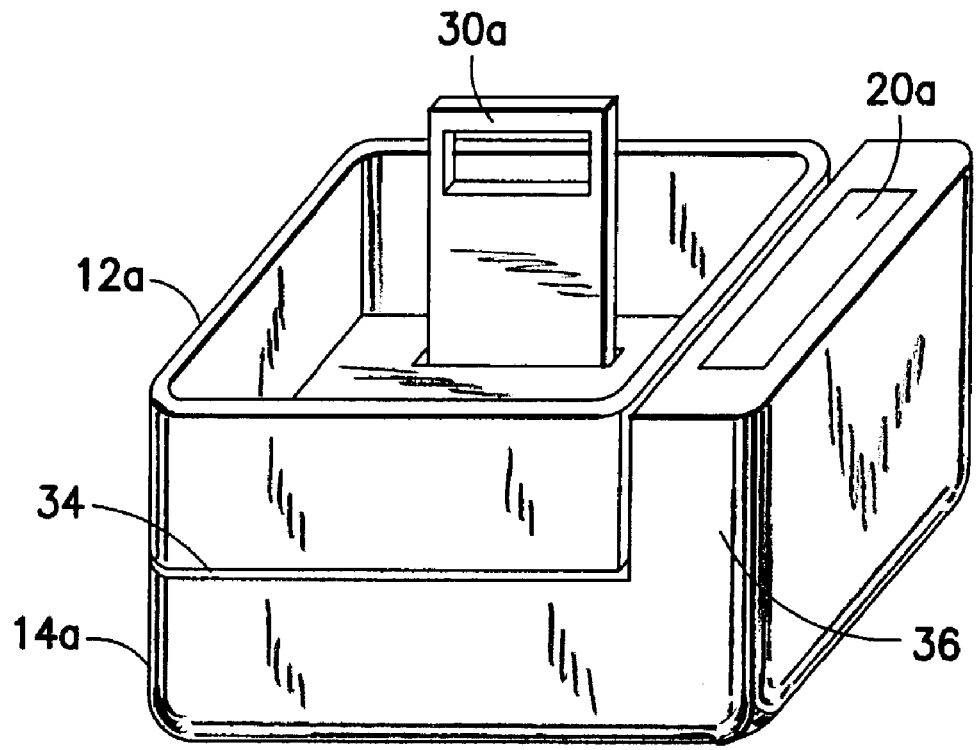
FIG. 6 is a schematic view of a medical waste disposal container and a carrier tray in accordance with a further embodiment of the present invention.

FIG. 6 illustrates another embodiment of the present invention. In this embodiment, carrier tray 12a is of a smaller area than medical waste disposal container 14a. Medical waste disposal container 14a has a platform area 34 and an elevated portion 36. Carrier tray 12a rests on platform area 34 and is planer with the top surface of elevated portion 36 of medical waste disposal container 14a. Medical waste disposal container 14a is interengagably and removably mated with carrier tray 12a. Medical waste disposal container 14a has integrated handle or carry handle 30a to hold and transport medical tray carrier 10a and acts in a similar manner as described above. In such an embodiment, carrier tray 12a need not include any opening for disposal of medical waste. Instead, elevated portion 36 of medical waste disposal container 14a has opening 20a located on a top surface of elevated portion 36. Medical waste is disposed of directly into medical waste disposal container 14a via the opening 20a on the top surface of elevated portion 36 of medical waste disposal container 14a. Upon filling, medical waste disposal container 14a is detached from carrier tray 12a and is exchanged for an empty medical waste disposal container.

Figure 7:
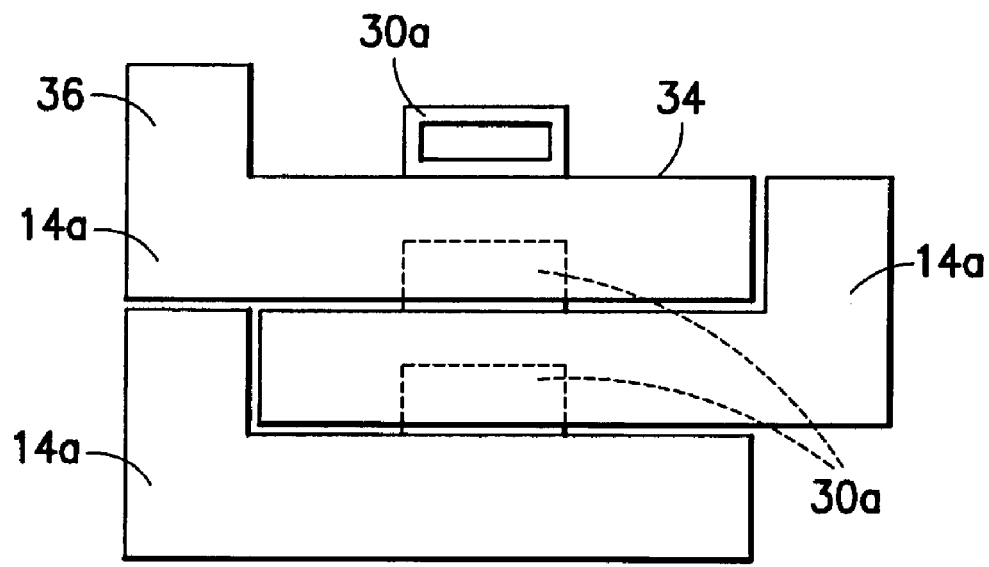
FIG. 7 is schematic view of a plurality of medical waste disposal containers shown in a stacked configuration.

Furthermore, a plurality of medical waste disposal containers 14a can be stacked upon each other, as illustrated in FIG. 7. This stacking arrangement allows for used and unused medical waste disposal containers to fit together and thus enables efficient storage and shipping of medical waste disposal containers for disposal or for use. Upon filling of medical waste disposal container 14a, carrier tray 12a is removed from medical waste disposal container 14a and handle 30a which is folded. Handle 30a therefore rests on top surface of platform area 36 of medical waste disposal container 14a. Medical waste disposal container 14a may additionally have a cavity in the bottom surface to mate with the folded handle of another medical waste disposal container. Therefore, when one medical waste disposal container is placed atop another medical waste disposal container, the foldable handle in the bottom medical waste disposal container fits into the handle cavity in the bottom surface of the top medical waste disposal container, thereby allowing for a connecting fit. Additional medical waste disposal containers can be stacked in the same fashion. As shown in FIG. 7, the medical waste disposal containers are alternated in position such that all platform areas of medical waste disposal containers are stacked upon each other, while elevated portions 36 of medical waste disposal containers 14a are alternated.

Figure 8:
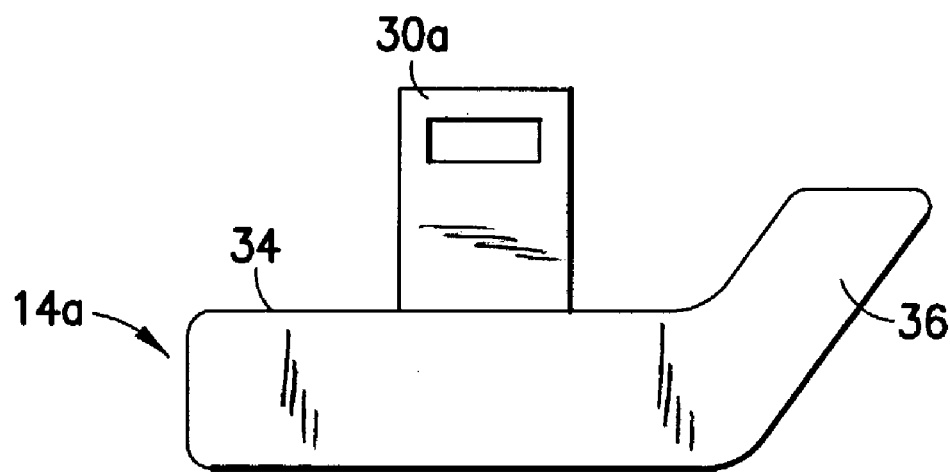
FIG. 8 is a schematic view of a medical waste disposal container in accordance with yet a further embodiment of the present invention.
Figure 9:
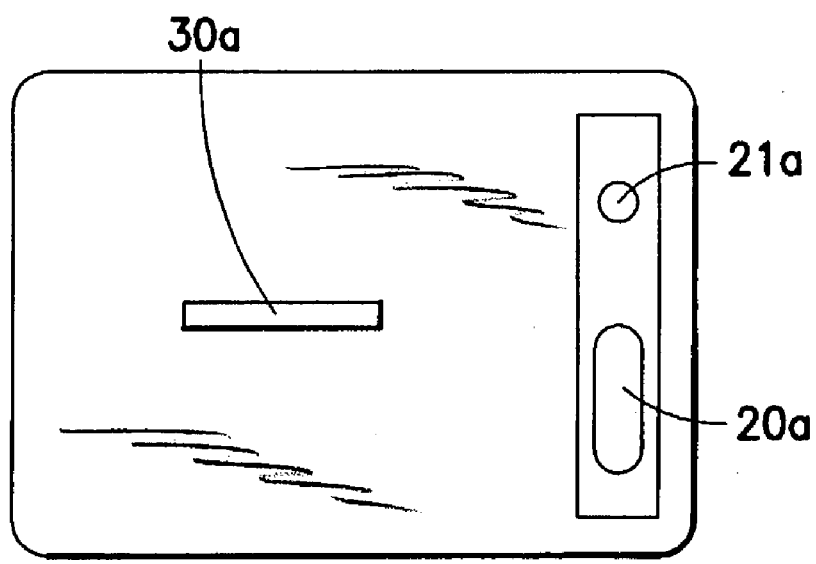
FIG. 9 is a schematic top view of a medical waste disposal container in accordance with another embodiment of the present invention.

Medical waste disposal container 14a can be of any configuration to promote easy use. For example, as shown in FIG. 8, medical waste disposal container 14a can be at any angle to form a chute-like shape. The medical waste is dropped through opening 20a at the top of the chute, and travels along the length of the chute until it reaches the bottom of the medical waste disposal container 14a for storage. Opening 20a at the top of the chute can be wide or narrow depending on the desired configuration. Additionally, there may be more than one opening, as illustrated in FIG. 9. FIG. 9 shows a top view of medical waste disposal container 14a with more than one controlled opening. For example, medical waste disposal container 14a can have a first opening 20a for large medical waste and a separate second opening 21a smaller in size for smaller medical waste. Furthermore, openings 20a and 21a do not need to be located adjacent to each other but can be located anywhere in medical waste disposal container 14a. It is further contemplated that such an arrangement with a plurality of openings can also be incorporated to the medical carrier transport 10 discussed above with respect to FIGS. 1–5, with the carrier tray including corresponding openings for corresponding engagement with each opening in the medical waste disposal container to provide a connecting passageway therewith.

While the present invention is satisfied by embodiments in many different forms, there is shown in the FIGS. and described herein in detail, the preferred embodiments of the invention, with the understanding that the present disclosure is to be considered as exemplary of the principles of the invention and is not intended to limit the invention to the embodiments illustrated. Various other embodiments will be apparent to and readily made by those skilled in the art without departing from the scope and spirit of the invention. The scope of the invention will be measured by the appended claims and their equivalents.

The invention claimed is:

1. A medical transport carrier comprising:
    a carrier tray comprising a supply area adapted for containing medical supplies; and
    a medical waste disposal container mated with said carrier tray, said medical waste disposal container adapted for containing medical waste at a location remote from said supply area,
    wherein said medical waste disposal container is substantially closed and has an opening for receiving medical waste when said medical waste disposal container is mated with said carrier,
    wherein said medical waste container is mated to said carrier tray such that said medical waste container is detachable from said carrier tray;
    wherein said carrier tray has a carrier tray opening for disposing medical waste, and the carrier tray opening is resealable by a cover attached to the carrier tray,
    wherein said carrier tray opening forms a connecting passageway with the opening for receiving medical waste in said medical waste disposal container, and
    wherein the carrier is capable of receiving medical supplies when the carrier tray opening is covered.

2. The medical transport carrier as in claim 1, wherein said medical waste container and said carrier tray include corresponding structure for locking engagement therebetween.

3. The medical transport carrier as in claim 2, wherein one of said medical waste container or said carrier tray includes a latch and the other includes a rib for latching engagement therebetween.

4. The medical transport carrier as in claim 1, wherein said medical waste disposal container is located below said carrier tray.

5. The medical transport carrier as in claim 1, wherein said medical waste disposal container has an integrated handle which extends through said carrier tray.

6. The medical transport carrier as in claim 1, wherein said medical waste disposal container has a translucent surface.

7. A medical transport carrier comprising:
    a carrier tray having a supply area for containing medical supplies, and
    a medical waste disposal container being interengagable and removably matable with said carrier tray, and being a substantially closed structure having an opening adapted for receiving medical waste through said opening for containing medical waste at a location remote from said supply area of said carrier tray when said medical waste disposal container is mated with said carrier, wherein said medical waste container and said carrier tray include corresponding structure for locking engagement therebetween;

wherein the carrier tray has a carrier tray opening for receiving medical waste, and the carrier tray opening is resealable by a cover attached to the carrier tray;

wherein said medical waste disposal container has an opening for receiving medical waste, said opening forming a connecting passageway with said carrier tray opening; and wherein the carrier is capable of receiving medical supplies when the carrier tray opening is covered.

8. The medical transport carrier as in claim 7, wherein said medical waste disposal container has an integrated handle which extends through said carrier tray.

9. The medical transport carrier as in claim 7, wherein said medical waste disposal container has a translucent surface.

10. A medical transport carrier comprising:

a carrier tray comprising a supply area adapted for containing medical supplies, said carrier tray including an opening extending through a bottom surface of the carrier tray for disposing of medical waste; and a medical waste disposal container interchangeable with a bottom surface of said carrier tray, said medical waste disposal container having an opening for receiving medical waste, said opening in said medical waste disposal container connected with said opening in said carrier tray, wherein said carrier tray further includes an opening for receiving a carry handle; and said medical waste disposal container further includes a carry handle for receipt through said opening of said carrier tray adapted for receiving a carry handle.

11. The medical transport carrier as in claim 10, wherein said opening for receiving medical waste is adjacent said opening for receiving said carry handle.

12. The medical transport carrier as in claim 10, wherein said carry handle is foldable.

13. The medical transport carrier as in claim 10, wherein said medical waste disposal container has a protective cover.

\* \* \* \* \*